United States Patent
De Decker et al.

(10) Patent No.: US 6,852,881 B2
(45) Date of Patent: Feb. 8, 2005

(54) PURIFICATION METHOD FOR (METH) ACRYLIC ACID

(75) Inventors: Emile De Decker, Schoten (BE); Erik Bastiaensen, Kapellen (BE); Dieter Baumann, Walldorf (DE); Bernd Eck, Viernheim (DE); Jörg Heilek, Bammental (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/181,919

(22) PCT Filed: Jan. 24, 2001

(86) PCT No.: PCT/EP01/00743
§ 371 (c)(1),
(2), (4) Date: Jul. 26, 2002

(87) PCT Pub. No.: WO01/55076
PCT Pub. Date: Aug. 2, 2001

(65) Prior Publication Data
US 2003/0018214 A1 Jan. 23, 2003

(30) Foreign Application Priority Data
Jan. 27, 2000 (DE) .................................. 100 03 498

(51) Int. Cl.$^7$ ................................................ C07C 51/42
(52) U.S. Cl. ...................................................... 562/600
(58) Field of Search ......................................... 562/600

(56) References Cited

U.S. PATENT DOCUMENTS 5,831,124 A    11/1998    Machhammer et al.

FOREIGN PATENT DOCUMENTS

| | | |
|---|---|---|
| DE | 100 03 497 | 4/2001 |
| EP | 0 616 998 | 9/1994 |
| WO | 98/01415 | 1/1998 |

*Primary Examiner*—Paul A. Zucker
(74) *Attorney, Agent, or Firm*—Oblon, Spivak, McClelland, Maier & Neustadt, P.C.

(57) ABSTRACT

(Meth)acrylic acid is purified by crystallization by a process in which the (meth)acrylic acid is purified by a combination of at least two different dynamic crystallization processes, in particular a suspension crystallization and a layer crystallization.

21 Claims, 4 Drawing Sheets

PURIFICATION METHOD FOR (METH) ACRYLIC ACID

BACKGROUND OF THE INVENTION

1. Field of the Invention

The present invention relates to a purification process which is suitable both for methacrylic acid and for acrylic acid. Below, the term (meth)acrylic acid means methacrylic acid or acrylic acid.

2. Description of the Background

Acrylic acid is a key chemical. Owing to its very reactive double bond and the acid function, it is particularly suitable as a monomer for the preparation of polymers. The greater part of the amount of acrylic acid monomers produced is esterified prior to polymerization—to give, for example, adhesives, dispersions or finishes. Only the smaller part of the acrylic acid monomers produced is polymerized directly—to give, for example, superabsorbers. While monomers of high purity are generally required in the direct polymerization of acrylic acid, the requirements relating to the purity of the acrylic acid are not so high when it is esterified prior to polymerization.

It is generally known that acrylic acid can be prepared by gas-phase oxidation of propene with molecular oxygen under heterogeneous catalysis over solid catalysts at from 200 to 400° C., in two stages via acrolein. Here, oxidic multicomponent catalysts, for example based on oxides of the elements molybdenum, chromium, vanadium or tellurium, are used.

Several processes have been proposed for working up the gas mixture obtained in the catalytic gas-phase oxidation.

WO-A-9 801 415 discloses a process for the preparation of (meth)acrylic acid in which the gas mixture obtained by catalytic gas-phase oxidation is condensed and (meth) acrylic acid can be crystallized from the resulting aqueous solution without addition of assistants.

EP-B-0 616 998 describes a process for purifying acrylic acid by means of fractional crystallization, the acrylic acid being purified by a combination of dynamic and static crystallization in a plurality of stages by means of crystallization/melting cycles, and the residue of the dynamic crystallization being further concentrated by the static crystallization. The dynamic crystallization described is either a falling-film layer crystallization or a suspension crystallization.

SUMMARY OF THE INVENTION

It is an object of the present invention to provide a process for purifying (meth)acrylic acid which permits particularly economical working-up for a wide concentration range of the acids crystallizing and a wide yield range.

We have found that this object is achieved by the combination of at least two different dynamic crystallization processes.

The present invention therefore relates to a process for purifying (meth)acrylic acid by crystallization, wherein the (meth)acrylic acid is purified by a combination of at least two different dynamic crystallization processes. Preferred embodiments of the invention are described in the following description, the Figures, the Example and the subclaims.

DETAILED DESCRIPTION OF THE PREFERRED EMBODIMENTS

Figure 1A:
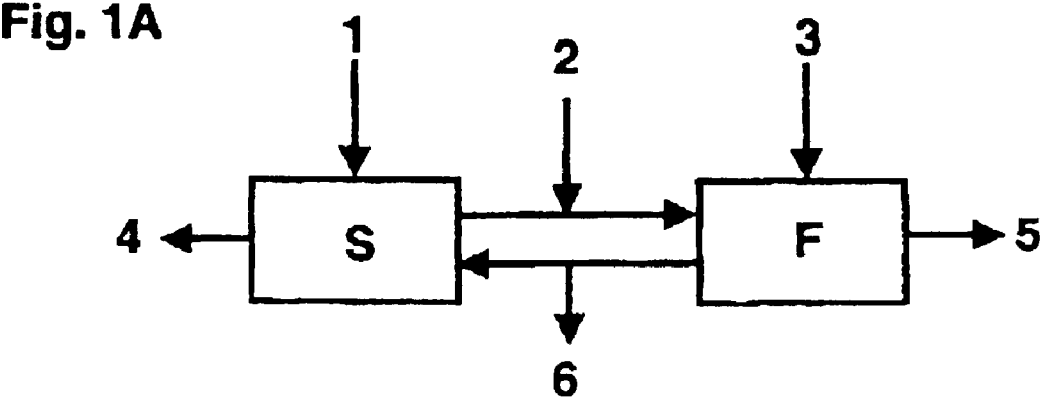
FIGS. 1A and B show preferred processes comprising suspension and layer crystallization.

Suitable mixtures from which the starting mixture for the present process can be obtained are preferably prepared by catalytic gas-phase oxidation of $C_3$- or $C_4$-alkanes, $C_3$- or $C_4$-alkenes, $C_3$- or $C_4$-alkanols and/or $C_3$- or $C_4$-alkanals and/or precursors thereof. The mixture is particularly advantageously prepared by catalytic gas-phase oxidation of propene, acrolein, tert-butanol, isobutene, isobutane, isobutyraldehyde, methacrolein, isobutyric acid or methyl tert-butyl ether. It is possible to use all precursors of said compounds, in which the actual $C_3/C_4$ starting compound is formed only as an intermediate during the gas-phase oxidation.

Methyl tert-butyl ether or isobutyric acid may be mentioned by way of example for the preparation of methacrylic acid.

The catalytic gas-phase oxidation of propene and/or acrolein to acrylic acid with molecular oxygen by known processes, for example according to DE-A-196 24 31, is particularly advantageous. Here, temperatures of from 200 to 450° C. and, if required, superatmospheric pressure are preferably employed. Preferably used heterogeneous catalysts are oxidic multicomponent catalysts based on oxides of molybdenum, bismuth and iron in the 1st stage (oxidation of propene to acrolein) and those based on the oxides of molybdenum and vanadium in the second stage (oxidation of acrolein to acrylic acid). If propane is used as a starting material, it can be reacted to give a propene/propane mixture by catalytic oxydehydrogenation, as described in U.S. Pat. No. 5,510,558, by homogeneous oxydehydrogenation, corresponding to CN-A-1 105 352, or by catalytic dehydrogenation, as described in EP-A-0 253 409. When a propene/propane mixture is used, propane acts as a diluent gas. Other suitable propene/propane mixtures are refinery propene (70% of propene and 30% of propane), or cracker propene (95% of propene and 5% of propane). In principle, propene/propane mixtures such as the abovementioned ones can be oxidized with oxygen or air or a mixture of oxygen and nitrogen of any composition to give acrolein and acrylic acid.

The reaction of propene to give acrylic acid is highly exothermic. The reaction gas, which advantageously contains an inert diluent gas, e.g. atmospheric nitrogen, or one or more saturated $C_1$-$C_6$-hydrocarbons, in particular methane and/or propane, and/or steam, in addition to starting materials and products, can therefore absorb only a small part of the heat of reaction. Although the type of reactors used is not subject to any restriction per se, tube-bundle heat exchangers filled with the oxidation catalyst are generally used since in these the predominant part of the heat liberated during the reaction can be removed by convection and radiation to the cooled tube walls.

In the catalytic gas-phase oxidation, it is not pure acrylic acid which is obtained but a gaseous mixture which contains essentially unconverted acrolein and/or propene, steam, carbon monoxide, carbon dioxide, nitrogen, propane, oxygen, acetic acid, propionic acid, formaldehyde, further aldehydes and maleic anhydride as secondary components in addition to the acrylic acid. Usually, the reaction product mixture contains from 1 to 30% by weight of acrylic acid, from 0.05 to 1% by weight of propene and from 0.05 to 1% by weight of acrolein, from 0.05 to 10% by weight of oxygen, from 0.05 to 2% by weight of acetic acid, from 0.01 to 2% by weight of propionic acid, from 0.05 to 1% by weight of formaldehyde, from 0.05 to 2% by weight of aldehydes, from 0.01 to 0.5% by weight of maleic anhydride and from 20 to 98, preferably from 50 to 98%, by weight of inert diluent gases, based in each case on the total reaction mixture. In particular, saturated $C_1$-$C_6$-hydrocarbons, such as from 0 to 90% by weight of methane and/or propane, as well as from 1 to 30% by weight of steam, from 0.05 to 15% by weight of oxides of carbon and from 0 to 90% by weight of nitrogen, based in each case on 100% by weight of diluent gas, are present as inert diluent gases.

The methacrylic acid can be prepared analogously to acrylic acid by catalytic gas-phase oxidation of $C_4$ starting compounds with molecular oxygen. The methacrylic acid is particularly advantageously obtainable by catalytic gas-phase oxidation of isobutene, isobutane, tert-butanol, isobutyraldehyde, methacrolein or methyl tert-butyl ether. The catalysts used are likewise catalysts comprising mixed oxides of transition metals (e.g. Mo, V, W and/or Fe). Particularly suitable processes are those in which the preparation is carried out starting from methacrolein, particularly when the methacrolein is produced by gas-phase catalytic oxidation of tert-butanol, isobutane or isobutene or by reaction of formaldehyde with propionaldehyde according to EP-B-0 092 097. Thus, it is also possible to prepare methacrylic acid in two stages by (1) condensation of propionaldehyde with formaldehyde (in the presence of a secondary amine as a catalyst) to give methacrolein and (2) subsequent oxidation of the methacrolein to methacrylic acid.

As in the preparation of acrylic acid, it is not pure methacrylic acid which is obtained but a gaseous mixture which can essentially contain unconverted methacrolein and/or steam, carbon monoxide, carbon dioxide, nitrogen, oxygen, acetic acid, propionic acid, further aldehydes and maleic anhydride as secondary components in addition to the methacrylic acid.

For the preparation of the starting mixture for the present process, the reaction product mixture described above can be subjected to a condensation, in particular a partial or total condensation, a solution being obtained. The condensation can be carried out in one or more stages by conventional processes, the type of condensation not being subject to any particular restriction. Advantageously, the condensation is carried out using a direct condenser, condensate produced being brought into contact with the hot gaseous reaction product. Suitable apparatuses for the condensation are in particular spray scrubbers, venturi scrubbers, bubble columns or apparatuses having sprayed surfaces.

The (meth)acrylic acid-containing starting mixture for the novel purification process is not subject to any particular restrictions. Expediently, it contains from 75 to 99.9, preferably from 90 to 99.7, particularly preferably from 95 to 99.5, % by weight, based in each case on 100% by weight of starting mixture, of (meth)acrylic acid. The remainder comprises water and further impurities, such as acids, aldehydes, in particular acrolein, acetic acid, propionic acid, diacrylic acid, maleic acid (anhydride) and the polymerization inhibitor phenothiazine.

According to the invention, the starting mixture is subjected to a combination of at least two different dynamic crystallization processes, i.e. at least two crystallization stages. Preferably, the dynamic crystallization stages combined with one another are carried out as a fractional crystallization. In fractional crystallization, all stages above the feed of the starting mixture, i.e. in the direction of purer mixtures, are usually referred to as purification stages and all other stages, i.e. below the feed of the starting mixture, are usually referred to as stripping stages. Expediently, multi-stage crystallization processes are operated according to the countercurrent principle, where the crystals of each stage, after separation from the mother liquor, are fed to the respective stage with the next highest purity while the crystallization residue, i.e. the mother liquor, is fed to the respective stage with the next lowest purity. According to the purity of the respective crystals, the crystallization stages are usually referred to as higher or lower crystallization stages. Accordingly, the stripping stage which produces the crystals or the mother liquor with the lowest purity is referred to as the lowest crystallization stage and the purification stage with the highest purity is referred to as the highest stage.

According to the invention, the number of crystallization stages used is not subject in principle to any restrictions. In particular, it is determined by the composition of the starting mixture, the desired purity of the end product and the desired yield. Advantageously, the fractional crystallization is carried out using at least one stripping stage and at least one purification stage.

The dynamic crystallization processes used according to the invention are in principle any crystallization process which is carried out with forced movement of the mother liquor. According to the invention, at least two different dynamic crystallization processes are used, the use of two different dynamic crystallization processes being particularly preferred. The type of dynamic crystallization processes used is not subject to any particular restrictions. Suitable processes are suspension crystallization, falling-film layer crystallization, layer crystallization of the type with full flow through a tube or layer crystallization on moving cooling surfaces (cooling belt, chill roll), a combination of suspension crystallization and falling-film layer crystallization being preferably used.

The novel process is not restricted with regard to the procedure for the dynamic crystallization processes used. These may be continuous or batchwise. Both suspension crystallization and layer crystallization can be operated continuously or batchwise. Preferably, the suspension crystallization and a layer crystallization are carried out continuously on moving cooling surfaces while the falling-film layer crystallization and the layer crystallization of the type with full flow through a tube are operated in particular batchwise. In a further preferred embodiment, a suspension crystallization is carried out below the layer crystallization. Particularly preferably, the suspension crystallization is used in the stripping section, in particular in all stripping stages, while the layer crystallization is preferably used in the purification section, in particular in all purification stages.

The removal of heat in the dynamic crystallization processes can preferably be effected by cooling apparatus walls or by partial evaporation of the crystallizing solution under reduced pressure. Particularly preferably, the heat is removed by indirect cooling by means of heat exchanger surfaces. All mixtures suitable for this purpose, in particular water/methanol or water/glycol mixtures, may be used as heat-transfer media.

Advantageously, the temperature of the mother liquor during the dynamic crystallization is from −30 to +15° C., in particular from −10 to +15° C., particularly preferably from −5 to +14° C.

The suspension crystallization is a crystallization process in which, from a generally solid-free, liquid multicomponent system, as starting material, which is present in solution or as a melt, single crystals are formed by heat removal in the mass of the starting material. The crystal suspension containing the mother liquor and the solid phase consisting of dispersed single crystals has to be agitated during the suspension crystallization process, for which purpose circulation by pumping or stirring is particularly suitable. Adhesion of crystals to surfaces is not necessary here and is even undesirable. Since the crystal suspension has to be agitated, the suspension crystallization is considered to be a dynamic crystallization process.

In the suspension crystallization by indirect cooling, the heat is removed by means of scraped-surface heat exchangers which are connected to a stirred kettle or to a container without a stirrer. The circulation of the crystal suspension is ensured here by means of a pump. It is also possible to remove the heat via the wall of a stirred kettle having a stirrer passing close to the wall. A further preferred embodiment in the case of the suspension crystallization is the use of cooling disk crystallizers, as produced, for example, by GMF (Gouda in the Netherlands). In a further suitable variant of the suspension crystallization by cooling, the heat is removed by means of conventional heat exchangers (preferably tube-bundle or plate-type heat exchangers). In contrast to scraped-surface heat exchangers, stirred kettles having stirrers passing close to the wall or cooling disks, these apparatuses have no means for avoiding crystal layers on the heat-transfer surfaces. If, during operation, a state in which the heat transfer resistance assumes too high a value owing to incrustation is reached, the operation is switched to a second apparatus. During the operating time of the second apparatus, the first apparatus is regenerated (preferably by melting off the crystal layer or flushing the apparatus with unsaturated solution). If too high a heat transfer resistance is reached in the second apparatus, the operation is switched back to the first apparatus, etc. This variant can also be operated with more than two apparatuses or cyclically. Moreover, the crystallization can be effected by conventional evaporation of the solution under reduced pressure.

All known solid-liquid separation methods are suitable for separating the solid-liquid mixture obtained after the dynamic crystallization. Preferably, the crystals are separated from the mother liquor by filtration, sedimentation and/or centrifuging. However, it is also possible to remove the mother liquor from then preferably stationary crystals, for example by allowing it to run off. Advantageously, the filtration, sedimentation or centrifuging is preceded by preliminary thickening of the suspension, for example by hydrocyclones. All known centrifuges which operate batchwise or continuously are suitable for the centrifuging. Single-stage or multistage reciprocating-conveyor centrifuges are particularly advantageously used. Scroll-conveyor centrifuges or helical-conveyor centrifuges (decanters) are also suitable. Filtration is advantageously carried out by means of suction filters, which are operated continuously or batchwise, with or without a stirrer, or by means of belt filters. In general, the filtration can be carried out under superatmospheric or reduced pressure. Further process steps for increasing the purity of the crystals or of the crystal cake can be provided during and/or after the solid-liquid separation. In a particularly advantageous embodiment of the invention, the separation of the crystals from the mother liquor is followed by single-stage or multistage washing and/or sweating of the crystals or of the crystal cake. The wash liquid used is not subject to any restriction here. Advantageously, however, washing is effected with pure product, i.e. with a liquid which contains the acid whose purity is higher than that of the mother liquor. Washing with water is also possible. Washing can be carried out in apparatuses customary for this purpose, such as wash columns, in which the removal of the mother liquor and the washing are carried out in one apparatus, in centrifuges, which can be operated in one or more stages, or in suction filters or belt filters. The washing can be carried out on centrifuges or belt filters in one or more stages, it being possible to transport the wash liquid counter currently to the crystal cake. Sweating for increasing the purity of the crystals, which involves local melting of contaminated regions, can also be provided. In the suspension crystallization, it is particularly preferable to carry out sweating on centrifuges or belt filters, but carrying out a combination of washing and sweating in one apparatus may also be suitable.

In a particularly suitable manner, the wash liquid used for the crystals of a given crystallization stage is the feed to the same crystallization stage. Preferably, the mass ratio of wash liquid to crystals is preferably set at from 0.1 to 1, particularly preferably from 0.2 to 0.6, kg of wash liquid to kg of crystals.

There are no restrictions with regard to carrying out the dynamic layer crystallization, preferably a falling-film layer crystallization or a layer crystallization of the type with full flow through a tube. The dynamic layer crystallization on stationary cooling surfaces can be carried out as follows. The crystals of the acid are applied to the cooling surface by bringing the cooling surface into contact with a liquid mixture which contains the acid to be purified and by forming the corresponding crystals by cooling the cooling surface. For the formation of the crystals, the cooling surface is preferably cooled to a temperature range from the dissolution temperature of the respective liquid mixture to 60 K below this, preferably to 40 K below this. On reaching the desired crystal mass, the cooling process is terminated. Thereafter, the uncrystallized residual liquid depleted with respect to the desired acid can be taken off and thus removed from the cooling surfaces or the crystals formed. The removal of the residual liquid can be effected by simply allowing it to run off or by pumping it away.

This can be followed by a wash step and/or sweating step. During the washing, the crystals grown on the cooling surfaces are brought into contact with a wash liquid and are separated again from the latter. Consequently, the residual liquid remaining on the crystals is exchanged for the preferably purer wash liquid. Particularly in the case of relatively long residence time of the wash liquid on the crystals, exchange of impurities between the purer wash liquid and less pure regions of the crystals by diffusion is also effected. A preferably used wash liquid is fresh liquid mixture, which contains the acid to be purified, or pure melt of the acid. During sweating, the temperature of the crystals on the cooling surface is increased, after removal of the residual liquid, to a value which is from the freezing point of the residual liquid depleted with respect to the desired acid to the melting point of the pure acid. The sweating is advantageous particularly when the crystals of the acid are present not as a compact crystal layer but as a porous, inclusion-rich heap. Thereafter, the crystals can be liquefied by heating and the resulting liquid enriched with desired acid can be removed, which can once again be effected, for example, by simply allowing it to run off or pumping it away. The liquefaction of the crystals is preferably effected in a temperature range from the melting point of the respective acid to 40 K above this, in particular to 20 K above this.

In a particular embodiment of the dynamic layer crystallization, liquid enriched with acid and remaining on the cooling surfaces as a residual film after the melting is partially or completely frozen to give seed crystals on the cooling surface, after which the crystallization is carried out again. The freezing to give seed crystals can also be carried out by applying seed crystals to the cooling surface prior to the crystallization, by a procedure in which the cooling surface is brought into contact, in a separate step, with a melt, solution or suspension of the acid which is purer compared with the liquid mixture to be separated, and subsequently separated therefrom, and corresponding seed crystals are then formed by cooling. Here too, the residual film remaining on the cooling surfaces is partially or completely frozen by decreasing the temperature at the surfaces.

The cooling surfaces which can be used in the dynamic layer crystallization are not subject to any restriction and may be of any desired shape. One or more cooling surfaces may be used. Preferably, cylindrical cooling surfaces, e.g. pipes, or flat cooling surfaces are used. Here, either the cooling surfaces can be completely immersed in the liquid from which the desired acid is to be purified or a trickle film of this liquid may flow over said cooling surfaces, e.g. a pipe through which there is full flow or through or over which a trickle film flows. The cooling surfaces may also be parts of a heat exchanger which are provided with a feed and a discharge.

Thus, a particular embodiment of the dynamic layer crystallization may be summarized as a batchwise process having the following sequence:

1. Cooling surface(s) and the liquid mixture which contains the acid to be purified are brought into contact;
2. the cooling surfaces are cooled so that crystals of the acid grow on the surfaces;
3. the cooling process is terminated on reaching a desired crystal mass;
4. the uncrystallized residual liquid having a lower content of desired acid is removed from the cooling surfaces or the crystals formed;
5. the crystals present on the cooling surfaces are melted off by increasing the temperature at the surfaces and the resulting liquid enriched in acid is removed from the surfaces; and
6. liquid remaining as a residual film on the surfaces and having a higher acid content can be partially or completely frozen as seed crystals for the next crystallization cycle by decreasing the temperature at the surfaces.

The dynamic layer crystallization can be used for both crystallization from the melt and that from solution. It is particularly suitable for crystallization from the melt.

Falling-film layer crystallization can be carried out, for example, as described in EP-B-0 616 998.

In a preferred embodiment of the novel purification process, the crystallization is combined with a static crystallization and/or a distillation stage. Here, preferably at least a part of the mother liquor from at least one stripping stage of the crystallization is further purified in a static crystallization and/or distillation, in particular the mother liquor from the lowest dynamic crystallization stage, preferably a suspension crystallization, being used. There are no restrictions with regard to carrying out the static crystallization; for example, it is possible to proceed as described in EP-B-0 616 998. When a distillation stage is used, preferably a part of the resulting distillation residue is removed and the top product formed is fed to one or more stripping stages of the crystallization which are below the stripping stage from which the mother liquor for the feed to the distillation stage was removed. That part of the mother liquor from the at least one stripping stage which is fed to the distillation stage is preferably from 5 to 100, in particular from 50 to 100, particularly preferably from 90 to 100, % by weight of the respective mother liquor.

It is possible in principle to use any distillation column for the distillation. The distillation, distillation stage or distillation step can be carried out in one or more stages. In a multistage or fractional distillation (also referred to as rectification), which is advantageously carried out in rectification columns, a column having sieve trays, e.g. dual-flow trays or crossflow sieve trays of metal, is used. The distillation can also be carried out by means of an evaporator and a downstream condenser. Here, thin-film evaporators in the form of downflow evaporators or thin-film evaporators having rotating wipers are particularly preferred. The condensers used are conventional condensers, these not being subject to any restrictions. Injection condensers are particularly preferred. In a one-stage distillation, a simple evaporator, for example a still, and a conventional condenser are expediently used.

The invention is explained in more detail with reference to drawings which show preferred embodiments of the invention. Here, identical reference symbols or reference numerals have the same meanings.

Figure 1B:
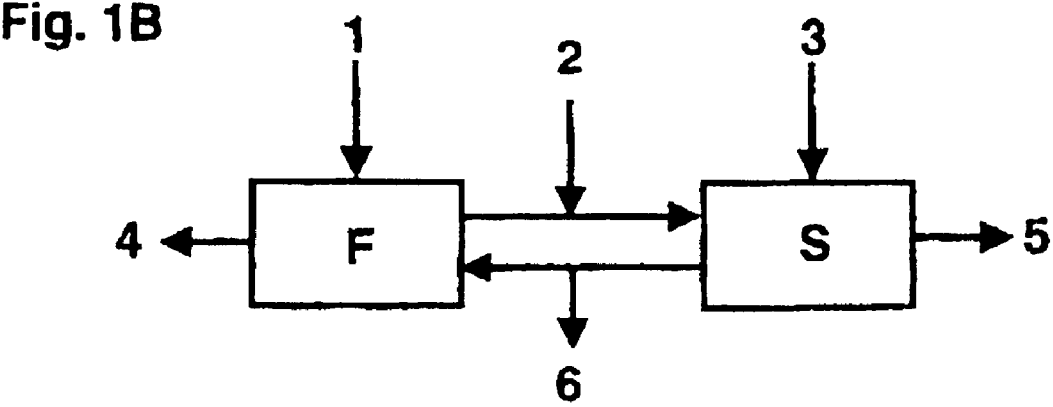

FIG. 1A shows an embodiment of crystallization which comprises a suspension crystallization S and a layer crystallization F, both of which can be carried out in one or more stages and continuously or batchwise. Here, the suspension crystallization S is arranged below the layer crystallization F. The reference numerals 1, 2 and 3 denote possible feeds for the starting mixture to be purified. The residue 4 is removed from the suspension crystallization S while the pure product 5 comprising the desired acid is removed from the layer crystallization F. FIG. 1B differs from FIG. 1A in that the layer crystallization is arranged below the suspension crystallization. The reference numeral 6 denotes a possible partial or complete removal of the mother liquor or of the residue of the upper dynamic crystallization.

Figure 2A:
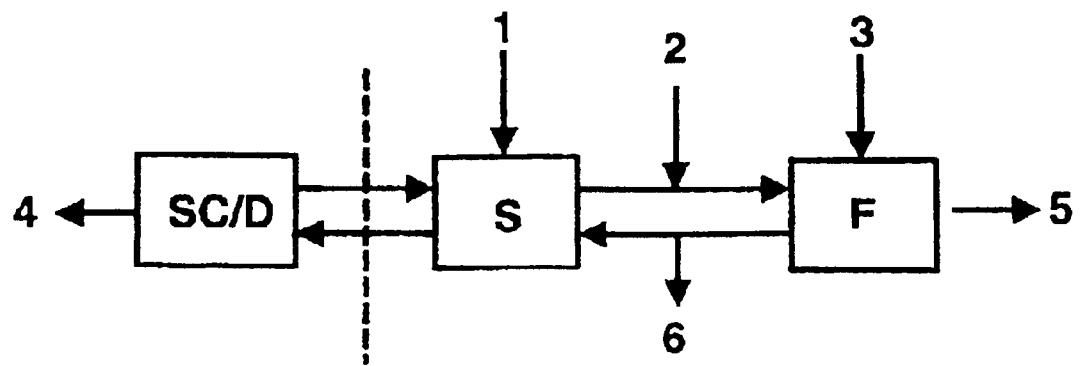
FIGS. 2A and B show preferred processes comprising additional static crystallization and/or distillation.
Figure 2B:
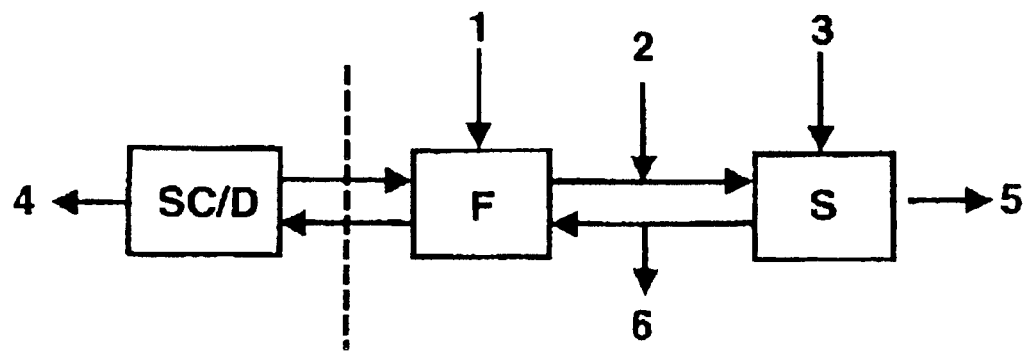

FIG. 2A and FIG. 2B show the embodiments of FIGS. 1A and 1B, respectively, which are supplemented by a static crystallization SC and/or a distillation stage D.

In this case, the residue 4 is removed from the static crystallization section and/or from the distillation section.

Figure 3A:
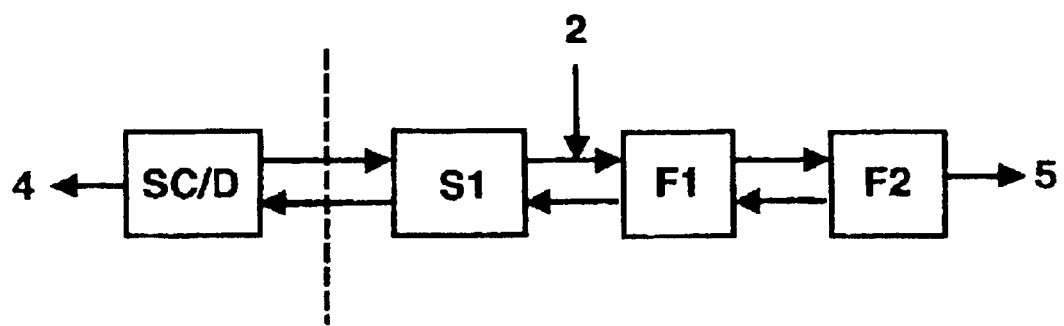
FIG. 3A shows a further preferred process comprising two layer crystallization stages, a suspension crystallization stage and static crystallization and/or distillation.

FIG. 3A shows a preferred arrangement of the novel process comprising a one-stage continuous suspension crystallization S1 as stripping stage and two batchwise falling-film crystallization stages F1 and F2 as purification stages. The residue of the suspension crystallization S1 is fed to a static crystallization SC and/or to a distillation stage D.

Figure 3B:
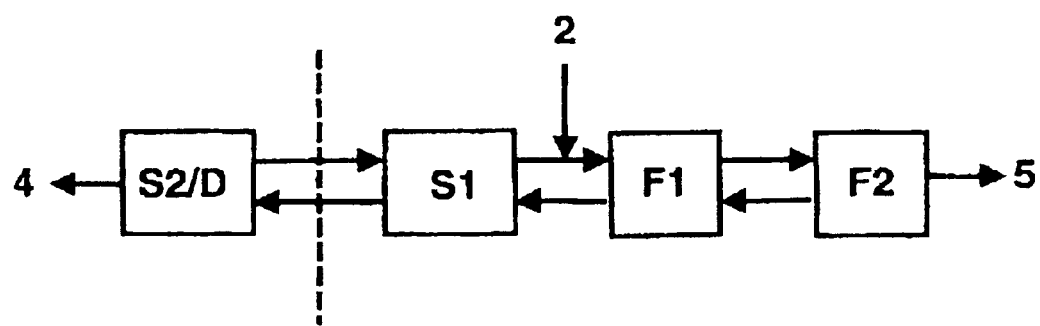
FIG. 3B shows a further preferred process comprising two layer crystallization stages, two suspension crystallization stages and a distillation.

FIG. 3B shows the same combination of the dynamic crystallization stages S1, F1 and F2 as FIG. 3A, the residue of stage S1 being fed to a combination of distillation and a further suspension crystallization stage S2, and preferably the suspension crystallization stage S2 being arranged below the distillation stage D.

Figure 4:
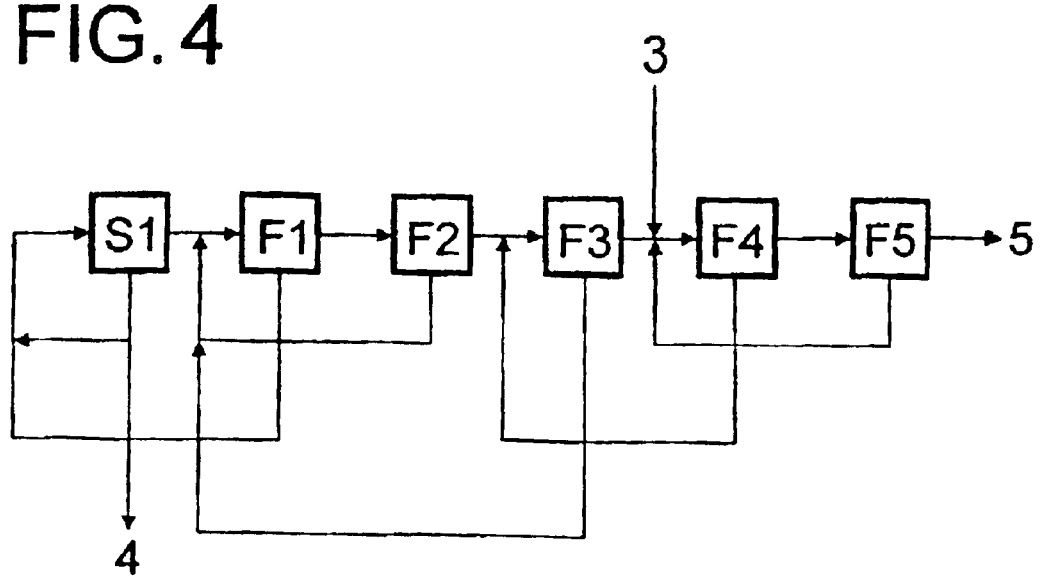
FIG. 4 shows a further preferred embodiment comprising a suspension crystallization stage and five layer crystallization stages.

FIG. 4 shows, as an embodiment of the invention, the fractional crystallization of an acrylic acid mixture, a total of 6 crystallization stages being used. Stage S1 is a one-stage continuous suspension crystallization, and all further stages are batchwise falling-film layer crystallization stages, as described, for example, in EP-B-0 616 998. The falling-film stages F1 to F3 are, like stage S1, stripping stages of the crystallization and stages F4 and F5 are purification stages of the crystallization.

By combining at least two different dynamic crystallization processes, the novel process makes it possible to obtain a pure acid in high yield in a very economical manner for a wide concentration range of starting acid. By means of the novel, suitable combination of dynamic processes, expensive crystallization stages can be omitted and the complexity of crystallization can be reduced. Particularly in comparison with a static crystallization, the dynamic crystallization processes have the advantage of a shorter residence time and a better purification effect per crystallization stage. In economic terms, the separation result is particularly good when suspension crystallization is arranged below the falling-film layer crystallization.

The novel process is furthermore explained in more detail with reference to the following Example, which constitutes a preferred embodiment of the invention.

EXAMPLE

A stream according to the starting composition shown in Table 1 was subjected to a six-stage fractional crystallization using an arrangement as shown in FIG. 4. After passing through the purification stages F4 and F5, a pure product having the composition shown in Table 1 was obtained. After passing through the stripping stages F3 to S1, a residue having the composition shown in Table 1 was obtained.

TABLE 1

|  | Starting mixture (stream 3) | Pure product (stream 5) | Residue (stream 4) |
| --- | --- | --- | --- |
| Acrylic acid | 99.45% by wt. | 99.97% by wt. | 52.96% by wt. |
| Acetic acid | 960 ppm | 147 ppm | 7.22% by wt. |
| Propionic acid | 330 ppm | 88 ppm | 2.15% by wt. |
| Diacrylic acid | 3100 ppm | 47 ppm | 27.46% by wt. |
| Water | 190 ppm | 23 ppm | 1.67% by wt. |
| Phenothiazine | 290 ppm | <1 ppm | 2.57% by wt. |
| Furan-II aldehyde | 220 ppm | <1 ppm | 1.95% by wt. |
| Others | 410 ppm | <5 ppm | 4.02% by wt. |

The feed to the suspension crystallization stage S1 was the mother liquor arriving from stage F1 and having the composition shown in Table 2. The crystals obtained in stage S1 had the composition shown in Table 2 and were fed to stage F1. The mother liquor obtained in stage S1 after the crystals had been separated off was partly removed as residue (stream 4) and had the residue composition shown in Table 1. That part of the mother liquor which was not removed was recycled to the crystallization. The mass ratio of removed to recycled mother liquor was 1:8. The suspension crystallization stage S1 was carried out in a stirred kettle having a stirrer passing close to the wall. The crystallization temperature was −8° C. The residence time of the suspension crystallization was 4 hours. The crystals produced were separated off on a screen centrifuge with a residence time of 1 minute on the centrifuge (basket diameter 200 mm, 2000 revolutions/minute). The filter cake was not washed.

TABLE 2

|  | Feed from F1 to S1 | Crystals in S1 |
| --- | --- | --- |
| Acrylic acid | 85.96% by weight | 93.45% by weight |
| Acetic acid | 2.92% by weight | 1.95% by weight |
| Propionic acid | 1.05% by weight | 0.8% by weight |
| Diacrylic acid | 7.32% by weight | 2.75% by weight |
| Water | 0.47% by weight | 0.2% by weight |
| Phenothiazine | 0.68% by weight | 0.26% by weight |
| Furan-II aldehyde | 0.52% by weight | 0.19% by weight |
| Others | 1.08% by weight | 0.4% by weight |

The acrylic acid yield achieved using the fractional crystallization was 99.4%.

The Example shows that, by means of the combination of two different dynamic crystallization processes, i.e. a suspension crystallization with falling-film layer crystallization, purification of acrylic acid is possible with high product purity and in particular with high yield of the purification process. The concentration of impurities in the residue (=high yield) is possible in the lowest stage even without washing or sweating of the crystals.

Compared with a residence time of 4 hours in the lowest crystallization stage in the process of the invention, the residence time in the crystallizer in each stage of the static crystallization during crystallization and sweating in the prior art according to EP-A-0 616 998 is from 8 to 9 hours. Thus, according to the invention, the residence time and, by omitting a stripping stage, the complexity of crystallization are reduced.

We claim:

1. A process for purifying (meth)acrylic acid by crystallization, which comprises:
   purifying a (meth)acrylic acid mixture by a combination of at least two different types of dynamic crystallization processes.

2. A process as claimed in claim 1, wherein the overall crystallization process occurs by fractional crystallization.

3. A process as claimed in claim 1, wherein the purifying occurs by employing two different dynamic crystallization processes.

4. A process as claimed in claim 1, wherein the overall crystallization process occurs by using at least one stripping stage and at least one purification stage.

5. A process as claimed in claim 1, wherein a starting mixture comprises from 75 to 99.9% by weight, based on 100% by weight of starting mixture, of (meth)acrylic acid.

6. A process as claimed in claim 1, wherein said combination of at least two different types of dynamic crystallization processes is combined with at least one method selected from static crystallization and a distillation.

7. A process for purifying (meth)acrylic acid by crystallization, which comprises:
   purifying a (meth)acrylic acid mixture by a combination of at least two different types of dynamic crystallization processes, and wherein the dynamic crystallization processes used are a suspension crystallization and a layer crystallization.

8. A process as claimed in claim 7, wherein the suspension crystallization process is carried Out continuously.

9. A process as claimed in claim 7, wherein the layer crystallization process is carried out batchwise.

10. A process as claimed in claim 7, wherein the overall crystallization process is carried out using at least one stripping stage and at least one purification stage.

11. A process as claimed in claim 7, wherein the suspension crystallization process is carried out below the layer crystallization.

12. A process as claimed in claim 7, wherein the overall crystallization process is carried out using at least one stripping stage and at least one purification stage, wherein all stripping stages are carried out as a suspension crystallization and all purification stages as a layer crystallization.

13. A process as claimed in claim 7, wherein the layer crystallization is carried out as a falling-film layer crystallization.

14. A process as claimed in claim 7, wherein a starting mixture comprises from 75 to 99.9% by weight, based on 100% by weight of starting mixture, of (meth)acrylic acid.

15. A process as claimed in claim 7, wherein said combination of at least two different types of dynamic crystallization processes is combined with at least one method selected from static crystallization and a distillation.

16. A process for purifying (meth)acrylic acid by crystallization, which comprises:

purifying a (meth)acrylic acid mixture by a combination of at least two different types of dynamic crystallization processes, wherein a first dynamic crystallization process is conducted in a dynamic crystallization device selected from the group consisting of a suspension crystallization device, a falling-film layer crystallizer, a layer crystallizer having a flow through tube and a layer crystallizer having moving cooling surfaces and a second dynamic crystallization process is conducted with one of said devices that is not selected as the device of the first dynamic crystallization process.

17. A process as claimed in claim 16, wherein the overall crystallization process occurs by employing fractional crystallization.

18. A process as claimed in claim 16, wherein the purifying occurs by employing two different dynamic crystallization processes.

19. A process as claimed in claim 16, wherein all stripping stages are carried out as a suspension crystallization and all purification stages as a layer crystallization.

20. A process as claimed in claim 16, wherein said combination of at least two different dynamic types of crystallization processes is combined with at least one method selected from static crystallization and a distillation.

21. A process as claimed in claims 16, wherein the overall crystallization process is carried out using at least one stripping stage and at least one purification stage.

* * * * *